US006923968B2

(12) United States Patent
Cantor

(10) Patent No.: US 6,923,968 B2
(45) Date of Patent: Aug. 2, 2005

(54) CYCLASE INHIBITING PARATHYROID HORMONE ANTAGONISTS OR MODULATORS AND OSTEOPOROSIS

(75) Inventor: Thomas L. Cantor, El Cajon, CA (US)

(73) Assignee: Scantibodies Laboratory, Inc., Santee, CA (US)

(*) Notice: Subject to any disclaimer, the term of this patent is extended or adjusted under 35 U.S.C. 154(b) by 293 days.

(21) Appl. No.: 09/928,047

(22) Filed: Aug. 10, 2001

(65) Prior Publication Data

US 2002/0160945 A1 Oct. 31, 2002

Related U.S. Application Data

(60) Provisional application No. 60/224,446, filed on Aug. 10, 2000.

(51) Int. Cl.$^7$ .............................................. A61K 39/00
(52) U.S. Cl. .................................... 424/198.1; 530/324
(58) Field of Search ........................ 424/198.1; 530/324

(56) References Cited

U.S. PATENT DOCUMENTS

| 4,369,138 A | | 1/1983 | Lindall .................... 260/112.5 |
| 4,423,037 A | | 12/1983 | Rosenblatt et al. ......... 424/177 |
| 4,508,828 A | | 4/1985 | Lindall et al. .............. 436/500 |
| 4,656,250 A | | 4/1987 | Morita et al. ............... 530/324 |
| 5,856,138 A | * | 1/1999 | Fukuda ..................... 435/69.4 |
| 6,030,790 A | | 2/2000 | Adermann et al. .......... 435/7.1 |
| 6,051,686 A | | 4/2000 | Krstenansky et al. ...... 530/333 |

FOREIGN PATENT DOCUMENTS

| DE | 33 47 548 | 7/1985 |
| DE | 44 34 551 | 4/1996 |
| EP | 0 783 522 | 12/2001 |
| WO | WO 91 06564 | 5/1991 |
| WO | EP 0 451 867 A1 * | 11/1991 |
| WO | WO 93 06845 | 4/1993 |
| WO | WO 94 03201 | 2/1994 |

OTHER PUBLICATIONS

Chorey et al., Biochemistry (1990) 29:1580–1586.
Hoare et al., Journal of Biological Chemistry (2000) 275(35):27274–27283.
International Search Report for PCT/US02/25348, mailed on Jul. 26, 2004, 4 pages.
Jonsson et al., Endocrinology (2001) 142(2):704–709.
Pausova et al., Mammalian Genome (1995) 6:408–414.
Takasu et al., Journal of Bone Mineral Metabolism (1994) 12(Suppl.1):S131–S134.
Yu et al., Endocrinology (1997) 138(8):3085–3092.
U.S. Appl. No. 09/231,422, filed Jan. 14, 1999.
U.S. Appl. No. 09/344,639, filed Jun. 26, 1999.
U.S. Appl. No. 09/928,047, filed Aug. 10, 2001.
U.S. Appl. No. 09/636,530, filed Aug. 10, 2001.
U.S. Appl. No. 09/636,531, filed Aug. 10, 2000.
U.S. Appl. No. 10/002,818, filed Nov. 2, 2001.
U.S. Appl. No. 60/224,396, filed Aug. 10, 2000.
U.S. Appl. No. 09/928,048, filed Aug. 10, 2001.
U.S. Appl. No. 09/323,606, filed Jun. 2, 1999.
Aldermann et al., in: Innovations and Perspectives in Solid Phase Synthesis, Epton (ed.). Mayflower World Wide, Birmingham (1994) pp. 429–432.
Atkinson et al., Journal of Immunoassay (1982) 3(1):31–51.
Blind et al., Clin. Chem. (1987) 33(8):1376–1381.
Bowie et al., Science (1990) 247:1306–1310.
Brossard et al., Journal of Clinical Endocrinology and Metabolism (1996) 81(11):3923–3929.
Campbell, Monoclonal Antibody and Immunosensor Technology, in Laboratory Techniques in Biochemistry and Molecular Biology, van der Vliet (ed.), Elsevier (1991) pp. 1–11, 42–45.
Caporale and Rosenblatt, Paraththyroid Hormone Antagonists Effective in vivo, in: Advances in Experimental Medicine and Biology, New York (1986) pp. 315–327.
Clinical Chemistry (1999) 45(6)Suppl:A97 b. Abstract Nos. 339–341.
D'Amour et al., Am. J. Physiol. (1986) 251:E680–E687.
Daniel et al., Virology (1994) 202:540–549.
Divieti, P. et al. (2001). *J Bone Miner Res* 2001:Suppl 1, S307.
Faugere, M.C. et al. (2001). *Kidney International* 60:1–460–1–468.
Faugere, M.C. et al. *Nephrology, Bone & Mineral Metabolism* A3995.
Fischer et al., The Journal of Clinical Investigation (1974) 54:1382–1394.
Gao et al., Clinica Chimica Acta (1996) 245:39–59.
Goodman, W. et al. (2000). *NEJM* 342:20, 1478–1483.

(Continued)

Primary Examiner—Lorraine Spector
Assistant Examiner—Dong Jiang
(74) Attorney, Agent, or Firm—Morrison & Foerster LLP

(57) ABSTRACT

The present invention relates to a novel method for treating a patient that has osteoporosis and the patient may be having administered cyclase activating parathyroid hormone (CAP) or analogues. The patient receives an administration of a cyclase inhibiting parathyroid hormone peptide (CIP) having an amino acid sequence from between (SEQ ID NO:1 [PTH$_{2-84}$]) and (SEQ ID NO:3 [PTH$_{34-84}$]) (i.e., a contiguous portion of PTH having an amino acid sequence set forth in SEQ ID NO:5 (PTH$_{1-84}$), having the N-terminal amino acid residue starting at any position spanning from position 2 through position 34 of the PTH$_{1-84}$, and the C-terminal amino acid residue ending at position 84 of the PTH$_{1-84}$), (preferably (SEQ ID NO:2 [PTH$_{3-84}$]) and (SEQ ID NO:8 [PTH$_{28-84}$])), or a conservatively substituted variant thereof exhibiting parathyroid hormone (PTH) antagonist activity in a therapeutically effective, but non-toxic amount that reduces the occurrence of hypercalcemia or osteosarcoma in the patient resulting from the administration of CAP, and yet, through a CAP rebound effect, is effective in itself in the treatment of osteoporosis.

7 Claims, 2 Drawing Sheets

OTHER PUBLICATIONS

Gordon et al., Parathyroid Hormone Domain for Protein Kinase C Stimulation Located within Amphiphilic Helix, in: Peptides: Chemistry and Biology, Proceedings of the Twelfth American Peptide Symposium, Jun. 16–21, 1991. Cambridge, MA, Smith and Rivier (eds.) Escom Science Publishers (1992) pp. 37–39.

Hashimoto et al., Journal of Cardiovascular Pharmacology (1981) 3(4):668–676.

Hehrmann et al., Journal of Immunoassay (1980) 1(2):151–174.

John et al., Journal of Clinical Endocrinology and Metabolism (1999) 84(11):4287–4290.

LePage et al., Clin. Chem. (1998) 44:805–810.

Logue et al., Journal of Immunological Methods (1991) 137:159–166.

Mägerlein et al., Arzneim.–Forsch. Drug Res. (1998) 48(1):197–204.

Mägerlein et al., Arzneim.–Forsch. Drug Res. (1998) 48(11):783–787.

Mallette, Journal of Clinical Endocrinology and Metabolism (1980) 50(1):201–203.

Nakamura et al., Endocrinol. JPN (1981) 28(4):547–549.

Ngo et al., The Protein Folding Problem and Tertiary Structure Prediction. Merz et al., (eds.). Birkhäuser Boston (1994) pp. 492–495.

Niall et al., Proc. Natl. Acad. Sci. USA (1974) 71(2):384–388.

Nussbaum et al., Chemical Abstracts (1982) 96(5):181–192.

Pang et al., Pharmacol. Exp. Ther. (1981) 216(3):567–571.

Podbesek et al. (1983). *Endocrinology* 112(3):1000–1006.

Qi et al., Am. J. Kidney Dis. (1995) 26:622–631.

Quarles et al., J. Clin. Endocrinol. Metab. (1992) 75:145–150.

Stadler, Homologous Radioimmunoassay for Human Parathyroid Hormone (Residues 1–34) with Biotinylated Peptide as Tracer, in Calcium Regulating Hormones, Vitamin D Metabolites, and Cyclic AMP Assays and their Clinical Application, Schmidt–Gayk et al., (eds.). Berlin/Heidelberg, Springer, (1990) pp. 137–150.

Tampe et al., J. Immunoassay (1992) 13(1):1–13.

Visser et al., Acta Endocrinology (1979) 90:90–102.

Wingender et al., Structure–Function Relationship in Parathyroid Hormone in: Advances in Protein Design, International Workshop, Blöcker et al. (eds.). VCH (1988) pp. 167–176.

Zanelli et al., Journal of Immunoassay (1983) 4(2):175–206.

Zemplar package insert. Abbott Reference (1998), 06–9998–R1–Rev. Roche Laboratories.

* cited by examiner

Whole Human PTH (1-84)

(SEQ ID NO:5)

CYCLASE INHIBITING PARATHYROID HORMONE ANTAGONISTS OR MODULATORS AND OSTEOPOROSIS

This application claims priority to U.S. patent application Ser. No. 60/224,446, filed Aug. 10, 2000, under 35 U.S.C. § 119(e).

TECHNICAL FIELD

The present invention relates to a novel method for treating a patient that has osteoporosis and the patient may be having administered cyclase activating parathyroid hormone (CAP) or analogues. The patient receives an administration of a cyclase inhibiting parathyroid hormone peptide (CIP) having an amino acid sequence from between (SEQ ID NO:1 [$PTH_{2-84}$]) and (SEQ ID NO:3[$PTH_{34-84}$]) (i.e., a contiguous portion of PTH having an amino acid sequence set forth in SEQ ID NO:5 ($PTH_{1-84}$) having the N-terminal amino acid residue starting at any position spanning from position 2 through position 34 of the $PTH_{1-84}$, and the C-terminal amino acid residue ending at position 84 of the $PTH_{1-84}$), (preferably (SEQ ID NO:2 [$PTH_{3-84}$]) and (SEQ ID NO:8 [$PTH_{28-84}$])), or a conservatively substituted variant thereof exhibiting parathyroid hormone (PTH) antagonist activity in a therapeutically effective, but non-toxic amount that reduces the occurrence of hypercalcemia or osteosarcoma in the patient resulting from the administration of CAP, and yet, through a CAP rebound effect, is effective in itself in the treatment of osteoporosis.

BACKGROUND ART

Calcium plays an indispensable role in cell permeability, the formation of bones and teeth, blood coagulation, transmission of nerve impulse, and normal muscle contraction. The concentration of calcium ions in the blood is, along with calcitriol and calcitonin, regulated mainly by parathyroid hormone (PTH). Extracellular calcium levels are directly affected by PTH through calcium uptake in kidney tubule cells and calcium transport to or from bone. Although calcium intake and excretion may vary, PTH serves through a feedback mechanism to maintain a steady concentration of calcium in cells and surrounding fluids. When serum calcium lowers, the parathyroid glands secrete PTH, affecting the release of stored calcium. When serum calcium increases, stored calcium release is retarded through lowered secretions of PTH.

The complete or whole form of human PTH, (hPTH), is a unique 84 amino acid peptide (SEQ ID NO:5), as is shown in FIG. 1. Researchers have found that this peptide has an anabolic effect on bone that involves a domain for protein kinase C activation (amino acid residues 28 to 34) as well as a domain for adenylate cyclase activation (amino acid residues 1 to 7). However, various catabolic forms of clipped or fragmented PTH peptides also are found in circulation, most likely formed by intraglandular or peripheral metabolism, or example, hPTH can be cleaved between amino acids 34 and 35 to produce a (1-34) PTH N-terminal fragment and a (35-84) PTH C-terminal fragment. Likewise, clipping can occur between either amino acids 36 and 37 or 37 and 38. Recently, a large PTH fragment referred to as "non-(1-84) PTH" has been disclosed which is clipped closer to the N-terminal end of PTH. (See R. LePage et alia, "A non-(1-84) circulating parathyroid hormone (PTH) fragment interferes significantly with intact PTH commercial assay measurements in uremic samples " Clin Chem (1998); 44: 805–810.).

The cleaved fragments of PTH vary in both biological activity and metabolic clearance rate from the circulation. For example, the N-terminal human $PTH_{1-34}$ ($hPTH_{1-34}$) fragment has PTH agonist properties, but is rapidly removed from circulation. A daily subcutaneous administration of hPTH to patients with idiopathic osteoporosis has been shown to substantially increase their iliac trebecular bone volume. (See R. Podbesek et alia, "Effects of two treatment regimes with synthetic human parathyroid hormone fragment on bone formation and the issue balance of trabecular bone in greyhounds". Endocrinology (1983); 112: 1000–1006.)

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are particularly at risk for idiopathic osteoporosis (postmenopausal or Type I osteoporosis). Another high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, and oophorectomy.

In the various forms of osteoporosis, mechanical failure bone fractures frequently occur which are the result of bone loss. Postmenopausal osteoporosis is characterized by fractures of the wrist and spine, while femoral neck fractures seem to be the dominant feature of senile osteoporosis.

Bone loss in osteoporotics is believed to involve an imbalance in the process by which the skeleton renews itself This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. Resorption is followed by the appearance of osteoblasts (bone forming cells) that refill the cavity left by the osteoclasts with new bone.

In a healthy adult subject, the rate at which osteoclasts and osteoblasts are formed is such that bone formation and bone resorption are in balance constituting an optimal bone turnover rate. However, in osteoporotics an imbalance in the bone remodeling process develops which results in bone being lost at a rate faster than it is being made. Although this imbalance occurs to some extent in most individuals as they age, it is much more severe and occurs at a younger age in postmenopausal osteoporotics or following oophorectomy.

There have been many attempts to treat osteoporosis with the goal of either slowing further bone loss or, more desirably, producing a net gain in bone mass. Certain agents, such as estrogen and the bisphosphonates, appear to slow further bone loss in osteoporotics. Agents which slow bone loss, because of the different durations of bone resorption and formation, may appear to increase bone mass (on the order of 3% to 7%). However, this apparent increase is limited in time, not progressive, and is due to a decrease in "remodeling space." In addition, because of the close coupling between resorption and formation, impeding bone resorption also ultimately impedes bone formation.

Another class of agents investigated to combat the onset of osteoporosis encompasses PTH and PTH analogues. (See U.S. Pat. No. 6,051,686 to Kretenansky et alia, for example.) The theory behind the use of such compounds is to use the body's natural protein receptor binding process to counter a greater removal of calcium from bone than resorption of calcium. Unfortunately, such proposed treatments have had adverse effects, including hypercalcemia (elevated serum calcium) and the formation of osteosarcomas.

DISCLOSURE OF THE INVENTION

The present invention relates to a novel method for treating a patient that has osteoporosis. The patient may be having administered cyclase activating parathyroid hormone (CAP), commonly referred to simply as PTH, or CAP analogues. The patient receives administration of a cyclase inhibiting parathyroid hormone peptide (CIP) having an amino acid sequence from between (SEQ ID NO:1 [$PTH_{2-84}$]) and (SEQ ID NO:3 [$PTH_{38-84}$]) (i.e., a contiguous portion of PTH having an amino acid sequence set forth in SEQ ID NO:5 ($PTH_{1-84}$). having the N-terminal amino acid residue starting at any position spanning from position 2 through position 34 of the $PTH_{1-84}$, and the C-terminal amino acid residue ending at position 84 of the $PTH_{1-84}$), (preferably (SEQ ID NO:2 [$PTH_{3-84}$]) and (SEQ ID NO:8 [$PTH_{28-84}$])), or a conservatively substituted variant thereof exhibiting parathyroid hormone (PTH) antagonist activity in a therapeutically effective, but non-toxic amount that reduces the occurrence of hypercalcemia or osteosarcoma in the patient resulting from the administration of CAP. CIP also has the ability when administered alone to provide a therapeutic treatment for osteoporosis by means of the CAP rebound effect without hypercalcemia or osteosarcoma side effects. Administration can be either continuous or pulsatile, as in the administration of CAP.

BEST MODES FOR CARRYING OUT THE INVENTION

Figure 1:
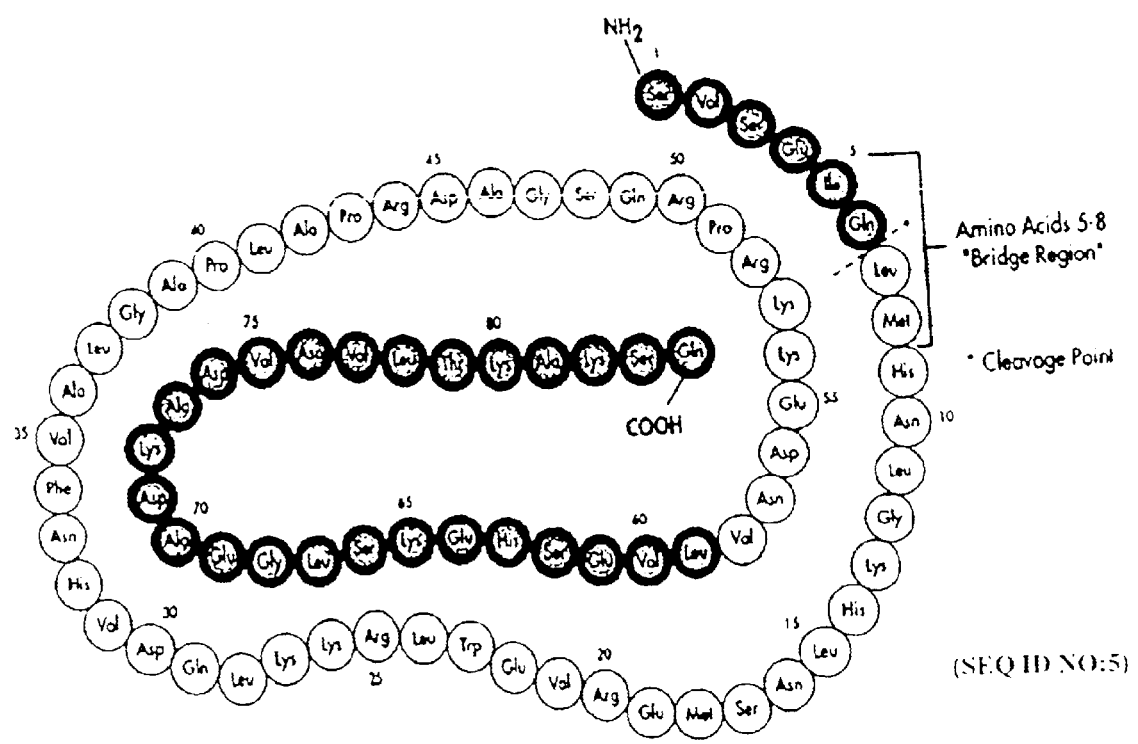
FIG. 1 is a diagrammatic view of hPTH (SEQ ID NO:5).

In disclosing the present invention, one should remember that there are a number of closely analogous, species dependent forms of PTH. The amino acid sequence of hPTH or CAP is shown in FIG. 1. However, for rat PTH, bovine PTH, or porcine PTH, for example, one finds the substitutions at some of the amino acids in the hPTH sequence. For the purposes of the present invention, one can use interchangeably truncated forms of these PTH's, although it is preferred to use a PTH having a sequence matching the species in which the PTH antagonist is used.

Preferred PTH antagonists of the present invention have an amino acid sequence from between $PTH_{2-84}$ (SEQ ID NO:1) and $PTH_{34-84}$ (SEQ ID NO:3) or a conservatively substituted variant thereof exhibiting PTH antagonist activity, with the most preferred form being from between $PTH_{3-84}$ (SEQ ID NO:2) and $PTH_{28-84}$ (SEQ ID NO:8).

PTH Antagonist Peptide Preparation

In order to make the present compositions, one can use any conventionally known method. For example, one can use recombinant DNA methods produce the desired compound.

Alternatively, one can use an automated peptide synthesizer, such as Model 431 made by Applied Biosystems, Inc. (Foster City, Calif., U.S.A.) Fmoc (9-fluoronylmethoxycarbonyl) can be used as the alpha-amino protecting group. All amino acids and solvents are available from Applied Biosystems and are of synthesis grade. Following synthesis, the peptide is cleaved from the resin, and side chains are de-blocked, using a cleavage cocktail containing 6.67% phenol, 4.4% (v/v) thioanisole and 8.8% ethanedithiol in trifluoroacetic acid (TFA). The cleaved peptide is precipitated and washed several times in cold diethyl ether. It is then dissolved in water and lyophilized. The crude peptide is subjected to amino acid analysis (Waters PICO-TAG System, Boston, Mass., U.S.A.) and reversed-phase HPLC using a VYDAC (TM) C8 column with 0.1% TFA in water and 99.9% acetonitrile in 0.1% TFA as the mobile buffers. The presence of a single major peak along with the appropriate amino acid composition is taken as evidence that the peptide is suitable for further use.

PTH Pharmaceutical Compositions

The present PTH antagonist peptides exhibit both oral and parenteral activity and can be formulated in solid or liquid dosage forms for oral, parenteral, intranasal, topical, or injectable administration using known carriers, excipients, or the like. The exact amount of present PTH antagonist used can vary depending upon the degree of antagonist property desired, the route of administration, or the duration of the treatment, as is known to the art.

Antagonist Properties

Figure 2:
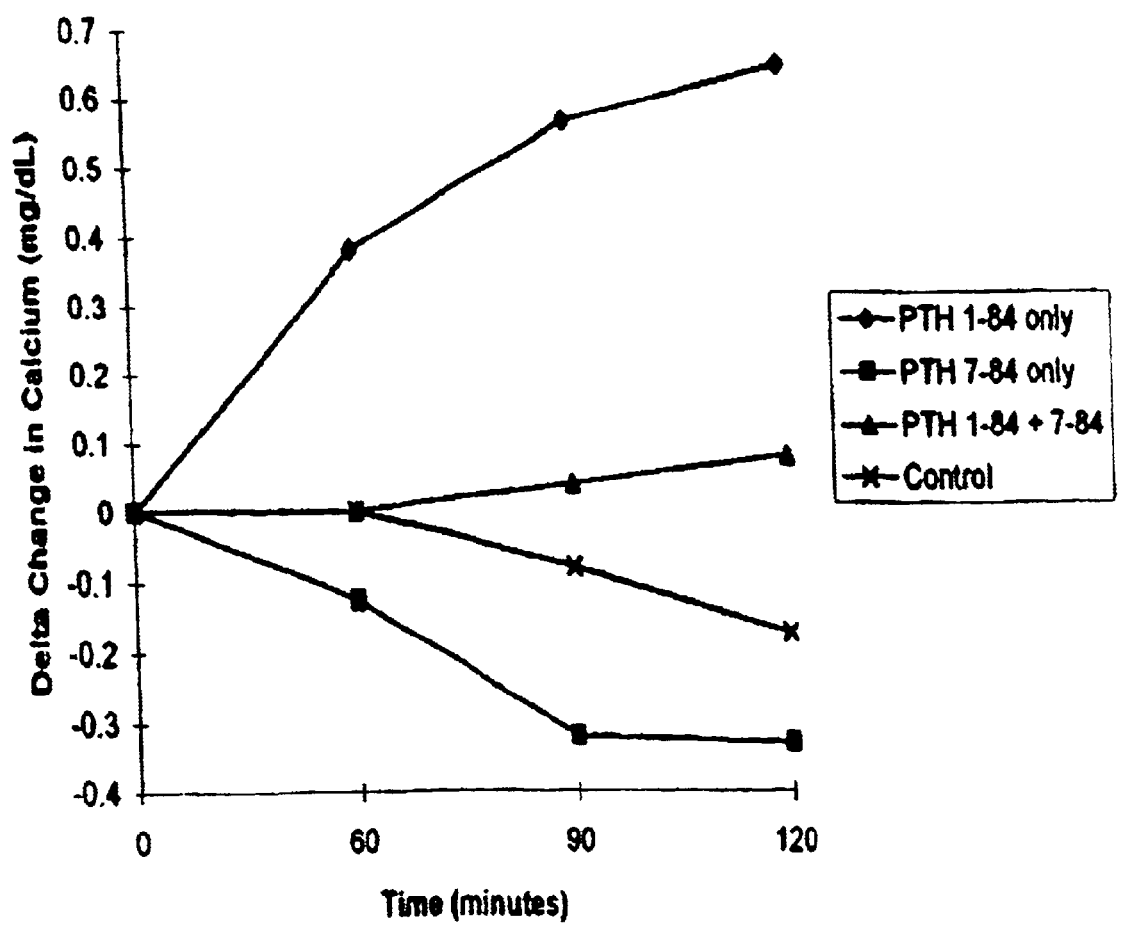
FIG. 2 is a graph showing the change in serum calcium using PTH alone, the present PTH antagonist alone, a combination of PTH and present PTH antagonist, and a control.

The present PTH antagonists have the ability to reduce the increase in serum calcium normally caused by PTH or a PTH agonist analog. These antagonists also possess an ability similar to CAP to treat osteoporosis due to the CAP rebound effect that comes with CIP administration. The CAP rebound effect is believed to be the body's response to an administration of CIP. This response occurs when the parathyroid gland cells secrete CAP in an effort to return the CAP/CIP ratio to homeostasis with the pre-CIP administration levels. PTH antagonist administration is not accompanied by hypercalcemia and osteosarcoma, as with direct CAP administration. FIG. 2 is a graph demonstrating such a hypercalcemic prevention property. Twenty-five rats were used in a demonstration of the effect of the present PTH antagonists. All of the rats had their parathyroid glands removed. Five rats received an i.v. injection of a saline control. The serum calcium of the control rats was measured and on average was lowered over time by about 0.18 mg/dl by virtue of a parathyroidectomy. Nine rats received an i.v. injection (10 μg/kg) of hPTH obtained from Bachem, A G of Bubendorf, Switzerland. The serum calcium of the hPTH rats was measured and on average was raised over time by about 0.65 mg/dl. Five rats received an equimolar i.v. injection of a $PTH_{7-84}$ (the PTH antagonist) also obtained from from Bachem, A G of Bubendorf, Switzerland. The serum calcium of the PTH antagonist rats was measured and on average was lowered over time by about 0.30 mg/dl. Finally, six rats received an i.v. injection comprised of hPTH (10 μg/kg) and an equimolar amount of the PTH antagonist $PTH_{7-84}$. The serum calcium of the hPTH/PTH antagonist rats was measured and on average remained substantially the same over time, raising only about 0.03 mg/dl. Thus, the present composition was able to prevent the substantial serum calcium increase normally associated with an administration of hPTH to rats having hypoparathyroidism, and quite unexpectedly, is much more potent in its antagonist property than the previously reported antagonist $PTH_{3-34}$.

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

I claim:

1. A method for reducing the occurrence of hypercalcemia or osteosarcoma in a patient,
   wherein said patient has osteoporosis and has received administration of, or is being administered, cyclase activating parathyroid hormone (CAP) or analogues thereof,
   said method comprising also administering a cyclase inhibiting parathyroid hormone peptide (CIP) to said patient in a therapeutically effective, but non-toxic amount,
   where said CIP comprises a contiguous portion of PTH having amino acid sequence set forth in SEQ ID NO:5 ($PTH_{1-84}$), said portion having an N-terminal amino acid residue starting at any position spanning from position 2 through position 34 of the $PTH_{1-84}$, and a C-terminal amino acid residue ending at position 84 of the $PTH_{1-84}$, or a conservatively substituted variant thereof exhibiting parathyroid hormone (PTH) antagonist activity.

2. The method of claim 1 wherein the CIP has an N-terminal amino acid residue starting at any position spanning from position 3 through position 28 of the $PTH_{1-84}$, and a C-terminal amino acid residue ending at position 84 of the $PTH_{1-84}$.

3. The method of claim 1, wherein the CIP administered is $PTH_{7-84}$.

4. The method of claim 1 wherein the CIP administration is performed in a pulsatile manner.

5. The method of claim 1, wherein the CIP is administered to reduce hypercalcemia.

6. The method of claim 1, wherein the CIP is administered to reduce osteosarcomas.

7. A method for reducing the occurrence of hypercalcemia or osteosarcoma in a patient,
   wherein said patient has osteoporosis and has received administration of, or is being administered, cyclase activating parathyroid hormone (CAP) or analogues thereof,
   said method comprising also administering a cyclase inhibiting parathyroid hormone peptide (CIP) to said patient in a therapeutically effective, but non-toxic amount,
   where said CIP comprises a contiguous portion of PTH having an amino acid sequence set forth in SEQ ID NO:5 ($PTH_{1-84}$), said portion having an N-terminal amino acid residue starting at any position spanning from position 2 through position 34 of the $PTH_{1-84}$, and a C-terminal amino acid residue ending at position 84 of the $PTH_{1-84}$.

* * * * *

SEQUENCE LISTING

<160> NUMBER OF SEQ ID NOS: 8

<210> SEQ ID NO 1
<211> LENGTH: 83
<212> TYPE: PRT
<213> ORGANISM: Homo sapiens

<400> SEQUENCE: 1

```
Val Ser Glu Ile Gln Leu Met His Asn Leu Gly Lys His Leu Asn Ser
 1               5                  10                  15

Met Glu Arg Val Glu Trp Leu Arg Lys Lys Leu Gln Asp Val His Asn
                20                  25                  30

Phe Val Ala Leu Gly Ala Pro Leu Ala Pro Arg Asp Ala Gly Ser Gln
            35                  40                  45

Arg Pro Arg Lys Lys Glu Asp Asn Val Leu Val Glu Ser His Glu Lys
        50                  55                  60

Ser Leu Gly Glu Ala Asn Lys Ala Asp Val Asn Val Leu Thr Lys Ala
 65                 70                  75                  80

Lys Ser Gln
```

<210> SEQ ID NO 2
<211> LENGTH: 82
<212> TYPE: PRT
<213> ORGANISM: Homo sapiens

<400> SEQUENCE: 2

```
Ser Glu Ile Gln Leu Met His Asn Leu Gly Lys His Leu Asn Ser Met
 1               5                  10                  15

Glu Arg Val Glu Trp Leu Arg Lys Lys Leu Gln Asp Val His Asn Phe
                20                  25                  30

Val Ala Leu Gly Ala Pro Leu Ala Pro Arg Asp Ala Gly Ser Gln Arg
            35                  40                  45

Pro Arg Lys Lys Glu Asp Asn Val Leu Val Glu Ser His Glu Lys Ser
        50                  55                  60

Leu Gly Glu Ala Asn Lys Ala Asp Val Asn Val Leu Thr Lys Ala Lys
 65                 70                  75                  80

Ser Gln
```

<210> SEQ ID NO 3
<211> LENGTH: 51
<212> TYPE: PRT
<213> ORGANISM: Homo sapiens

<400> SEQUENCE: 3

```
Phe Val Ala Leu Gly Ala Pro Leu Ala Pro Arg Asp Ala Gly Ser Gln
 1               5                  10                  15

Arg Pro Arg Lys Lys Glu Asp Asn Val Leu Val Glu Ser His Glu Lys
                20                  25                  30

Ser Leu Gly Glu Ala Asn Lys Ala Asp Val Asn Val Leu Thr Lys Ala
            35                  40                  45
```

-continued

Lys Ser Gln
    50

<210> SEQ ID NO 4
<211> LENGTH: 78
<212> TYPE: PRT
<213> ORGANISM: Homo sapiens

<400> SEQUENCE: 4

Leu Met His Asn Leu Gly Lys His Leu Asn Ser Met Glu Arg Val Glu
1               5                   10                  15

Trp Leu Arg Lys Lys Leu Gln Asp Val His Asn Phe Val Ala Leu Gly
            20                  25                  30

Ala Pro Leu Ala Pro Arg Asp Ala Gly Ser Gln Arg Pro Arg Lys Lys
        35                  40                  45

Glu Asp Asn Val Leu Val Glu Ser His Glu Lys Ser Leu Gly Glu Ala
    50                  55                  60

Asn Lys Ala Asp Val Asn Val Leu Thr Lys Ala Lys Ser Gln
65                  70                  75

<210> SEQ ID NO 5
<211> LENGTH: 84
<212> TYPE: PRT
<213> ORGANISM: Homo sapiens

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asn Lys Ala Asp Val Asn Val Leu Thr Lys
65                  70                  75                  80

Ala Lys Ser Gln

<210> SEQ ID NO 6
<211> LENGTH: 34
<212> TYPE: PRT
<213> ORGANISM: Homo sapiens

<400> SEQUENCE: 6

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 7
<211> LENGTH: 50
<212> TYPE: PRT
<213> ORGANISM: Homo sapiens

<400> SEQUENCE: 7

Val Ala Leu Gly Ala Pro Leu Ala Pro Arg Asp Ala Gly Ser Gln Arg
1               5                   10                  15

Pro Arg Lys Lys Glu Asp Asn Val Leu Val Glu Ser His Glu Lys Ser

-continued

```
                    20                  25                  30
Leu Gly Glu Ala Asn Lys Ala Asp Val Asn Val Leu Thr Lys Ala Lys
         35                  40                  45

Ser Gln
    50

<210> SEQ ID NO 8
<211> LENGTH: 57
<212> TYPE: PRT
<213> ORGANISM: Homo sapiens

<400> SEQUENCE: 8

Leu Gln Asp Val His Asn Phe Val Ala Leu Gly Ala Pro Leu Ala Pro
  1               5                  10                  15

Arg Asp Ala Gly Ser Gln Arg Pro Arg Lys Lys Glu Asp Asn Val Leu
             20                  25                  30

Val Glu Ser His Glu Lys Ser Leu Gly Glu Ala Asn Lys Ala Asp Val
         35                  40                  45

Asn Val Leu Thr Lys Ala Lys Ser Gln
    50                  55
```